United States Patent
Mast et al.

(10) Patent No.: US 8,540,724 B2
(45) Date of Patent: Sep. 24, 2013

(54) ANTERIOR DISTRACTOR-INSERTER WITH LINEAR COUNTERSINK ADJUSTMENT

(75) Inventors: Randall G. Mast, Denver, CO (US); Alan R. Burkholder, Denver, CO (US); G. Andrew Grim, Lascassas, TN (US)

(73) Assignee: Lanx, Inc., Broomfield, CO (US)

( * ) Notice: Subject to any disclaimer, the term of this patent is extended or adjusted under 35 U.S.C. 154(b) by 317 days.

(21) Appl. No.: 12/771,953

(22) Filed: Apr. 30, 2010

(65) Prior Publication Data
US 2011/0270261 A1   Nov. 3, 2011

(51) Int. Cl.
*A61B 17/88* (2006.01)
(52) U.S. Cl.
USPC .............................. 606/99; 606/105
(58) Field of Classification Search
USPC ............................ 606/99, 86 A, 86 B, 90, 105
See application file for complete search history.

(56) References Cited

U.S. PATENT DOCUMENTS

| 3,486,505 | A  | * | 12/1969 | Morrison | 606/90 |
| 6,478,800 | B1 | * | 11/2002 | Fraser et al. | 606/99 |
| 6,916,308 | B2 | * | 7/2005 | Dixon et al. | 604/122 |
| 7,722,622 | B2 | * | 5/2010 | Evans et al. | 606/99 |
| 7,896,884 | B2 | * | 3/2011 | Wing et al. | 606/90 |
| 2005/0090824 | A1 | * | 4/2005 | Shluzas et al. | 606/61 |
| 2005/0165408 | A1 | * | 7/2005 | Puno et al. | 606/99 |
| 2006/0195097 | A1 | * | 8/2006 | Evans et al. | 606/61 |
| 2006/0293684 | A1 | * | 12/2006 | Shluzas et al. | 606/90 |
| 2007/0185375 | A1 | * | 8/2007 | Stad et al. | 600/101 |
| 2008/0161817 | A1 | * | 7/2008 | Parsons et al. | 606/90 |
| 2008/0269764 | A1 | * | 10/2008 | Blain et al. | 606/99 |
| 2009/0048604 | A1 | * | 2/2009 | Milz et al. | 606/99 |
| 2009/0209967 | A1 | * | 8/2009 | Evans et al. | 606/99 |
| 2009/0234362 | A1 | * | 9/2009 | Blain et al. | 606/90 |

* cited by examiner

*Primary Examiner* — Kevin T Truong
*Assistant Examiner* — Zade Coley
(74) *Attorney, Agent, or Firm* — Perkins Coie LLP

(57) ABSTRACT

An embodiment of a method includes selecting a countersink depth setting with a linear countersink adjustment mechanism of a distractor-inserter, positioning distal ends of blades of the distractor-inserter between the two vertebral bodies to be separated, driving a head block assembly of the distractor-inserter forward until the retraction members of the distractor-inserter engages respective outer faces of the vertebral bodies, and retracting the distal ends of the blades and the tip from between the vertebral bodies, wherein the vertebral bodies compress the disc implant and hold the disc implant between the vertebral bodies at the countersink depth. A distractor-inserter includes first and second retraction members disposed within channels of the blades, and a countersink adjustment mechanism configured to linearly adjust a distance between a tip and the retraction members to thereby linearly adjust a countersink depth of an implantable element inserted between two distracted elements.

9 Claims, 14 Drawing Sheets

ANTERIOR DISTRACTOR-INSERTER WITH LINEAR COUNTERSINK ADJUSTMENT

BACKGROUND

A distractor-inserter is a device that can be used to distract (e.g., separate) two elements and insert another element between the two separated elements. For example, in the field of spinal medicine, a distractor-inserter is commonly used to separate two vertebrae and insert a spinal implant therebetween. The implant facilitates bone growth between the two vertebrae to thereby reduce back pain caused by a degenerated disc or other condition.

Distraction and insertion typically can be through an anterior approach (i.e., through the front of the patient) or a posterior approach (i.e., through a back side of the patient). When a surgeon uses a distractor-inserter, the surgeon inserts blades of the distractor-inserter into a cavity in the patient's body, positioning the blades between the two vertebrae to be distracted. The blades are then separated to distract or separate the vertebrae apart to create room for the implant to be inserted. After distracting the two vertebrae, the distractor-inserter is manipulated to insert the implant between the distracted vertebrae.

Typically, and particularly in the case of anterior distraction-insertion, there is very little room for a doctor to work within a patient's body during the distraction-insertion process. During the distraction-insertion process it is preferable that the distractor-inserter has minimal contact and interference with the patient's internal organs and vasculature to minimize trauma to the patient.

BRIEF SUMMARY

Embodiments presently disclosed generally relate to a distractor-inserter. More specifically, embodiments relate to an anterior distractor-inserter providing linear countersink depth adjustment. The countersink depth can be set to a value within a range of values, which may include more than two values. Adjustment may be analog, where any value within the range can be selected, or discrete, where whole values within the range can be selected. Embodiments may further include constant height retraction members. Further still, embodiments may include a ratchet mechanism that allows for automatic forward motion, but prevents backward motion unless the ratchet is manually disengaged.

An embodiment of a distractor-inserter includes a handle forming a passage disposed along a longitudinal axis, a drive shaft disposed along the longitudinal axis through the passage and moveable along the longitudinal axis, and a drive shaft grip coupled to a proximate end of the drive shaft and configured for use in imparting motion to the drive shaft. The distractor-inserter further includes first and second blades having respective first ends connected to the handle and respective second ends that can be opened, the first and second blades being curved away from the longitudinal.

Further still, an embodiment of the distractor-inserter includes a head block assembly coupled to a distal end of the drive shaft and disposed within the space between the first and second blades. The head block assembly is moveable along the longitudinal axis in response to movement of the drive shaft, wherein movement toward the second ends of the blades causes the second ends to open. The head block assembly includes first and second retraction members projecting in opposite directions away from the longitudinal axis and disposed within respective first and second elongate channels of the first and second blades.

Still further, an embodiment of the head block assembly includes a countersink adjustment mechanism including a tip at a distal end. The countersink adjustment mechanism is configured to linearly adjust a distance between the tip and the first and second retraction members to thereby linearly adjust a countersink depth of an implantable element pushed by the tip to a position between two distractable elements separated by the second ends of the first and second blades when the second ends are opened. The countersink adjustment mechanism may be configured to linearly adjust the countersink depth within a range including more than two depths. Still further, the countersink adjustment mechanism may provide analog adjustment of the countersink depth. Further yet, the countersink adjustment mechanism may provide stepwise adjustment of the countersink depth.

Still further, the range of countersink depths may comprise a lower limit of zero millimeters, and wherein a countersink depth of zero millimeters corresponds to an outer face of the implantable element being substantially flush with one or both outer faces of the two distractable elements. The first and second retraction members may be slidable along the respective first and second elongate channels of the first and second blades, and remain at a generally constant height relative to the respective first and second blades, regardless of their locations along lengths of the first and second blades.

An embodiment of a handle of a distractor-inserter includes a ratchet mechanism that includes an arm mounted on a pivot pin within the handle. Catch members are disposed on a first end of the arm and facing the drive shaft to engage threads of the drive shaft. The catch members allow for forward linear movement of the drive shaft but prevent backward linear movement of the drive shaft. The catch members may further allow forward and backward rotational movement of the drive shall. The ratchet mechanism may further include a push button on a second end of the arm and exposed on the handle. The push button is depressable to cause the arm to pivot about the pivot pin to disengage the catch members from the threads of the drive shaft. Disengagement of the catch members allows for backward linear movement of the drive shaft.

An embodiment of a countersink adjustment mechanism includes a countersink member carriage disposed along the longitudinal axis, a countersink member slidably coupled to the countersink member carriage, the countersink member having a distal end including the tip, and a countersink adjustment shall disposed through the passage in the countersink member carriage and coupled to the countersink member. At least a portion of the countersink adjustment shaft is threaded. The countersink adjustment mechanism further includes a countersink adjustment interface configured to engage the threaded portion of the countersink adjustment shaft to thereby cause longitudinal movement of the countersink adjustment shaft to impart corresponding longitudinal movement on the countersink member. The distractor countersink member may form a sleeve around the countersink member carriage. The countersink adjustment interface may include a thumbwheel.

An embodiment of a method of performing a distraction-insertion procedure includes selecting a countersink depth setting with a linear countersink adjustment mechanism of a distractor-inserter. Setting the countersink depth may include linearly adjusting a longitudinal distance between retraction members of the distractor-inserter and a tip configured to push an implant between two vertebral bodies. The method further includes positioning distal ends of blades of the distractor-inserter between the two vertebral bodies to be separated and driving a head block assembly of the distractor-inserter forward until the retraction members of the distractor-inserter engage respective outer faces of the vertebral bodies, wherein driving the head block assembly forward causes the distal ends of the blades to open, thereby separating the vertebral bodies, and wherein driving the head block assembly forward further comprises pushing the tip to a countersink depth between the vertebral bodies corresponding to the countersink depth setting. The method may further include retracting the distal ends of the blades and the tip from between the vertebral bodies, wherein the vertebral bodies hold the disc implant between the vertebral bodies at the selected countersink depth.

In an embodiment of a method, selecting the countersink depth setting includes adjusting the countersink depth adjustment interface. Selecting the countersink depth setting may include selecting a countersink depth from among a linear range of countersink depths. The linear countersink adjustment mechanism may include markings indicating a linear range of available countersink depths.

An embodiment of an apparatus for distracting two distractable elements and inserting an implantable element therebetween includes an elongate handle, first and second blades having respective proximal ends connected to a distal end of the elongate handle, and respective distal ends configured to distract the two distractable elements. The apparatus further includes a longitudinally moveable drive shaft disposed through a passage formed by the elongate handle and a head block assembly mounted on a distal end of the drive shaft and disposed within a space formed between the first and second blades. The head block assembly includes a tip configured to push the implantable element to a selected depth between the distracted elements, first and second retraction members slidably disposed within respective first and second channels of the first and second blades, wherein the first and second retraction members are configured to engage respective outer faces of the distracted elements, and means for linearly adjusting a distance between the tip and the first and second retraction members to thereby linearly adjust a countersink depth of the implantable element between the distracted elements.

In an embodiment of the apparatus, the means for linearly adjusting the distance between the tip and the retraction members includes a countersink member carriage having a first passage disposed therethrough along a longitudinal axis, a countersink member moveably coupled to the countersink member carriage and having a distal end comprising the tip, a thumbwheel having a second passage disposed therethrough along the longitudinal axis, the second passage having a threaded surface, and a countersink adjustment shaft disposed along the longitudinal axis and extending through the first passage and the second passage. The countersink adjustment shaft has a distal end coupled to the countersink member and a proximal end that is threaded. The threaded surface of the second passage engage with threads of the countersink adjustment shaft, and rotation of the thumbwheel causes longitudinal movement of the countersink adjustment shaft. Longitudinal movement of the countersink adjustment shaft causes corresponding longitudinal movement of the countersink member.

Further still, the distal end of the drive shaft may be twistably coupled to the head block assembly. The handle may include a ratchet mechanism configured to engage the drive shaft to prevent backward linear movement of the drive shaft unless the ratchet mechanism is disengaged from the drive shaft. The ratchet mechanism may permit forward linear movement when engaged with the drive shaft. The first and second retraction members may remain at a constant height relative to the respective first and second blades as the first and second retraction members slide along a length of the respective first and second blades. The countersink member carriage may include markings indicating a range of selectable countersink depths. The countersink member may include a sleeve around the countersink member carriage. The sleeve may expose countersink depth markings on the countersink member carriage as the sleeve moves forward. In some embodiments, the distal end of at least one of the blades has a friction element adapted to engage a face of the distractable element. This friction element may be shaped to generally match at least a portion of the distractable element face. In a particular embodiment, the distractable element is a vertebra, and the friction element is shaped to generally match at least a portion of the end plate of the vertebra.

This summary provides only a general outline of some embodiments disclosed herein. Many other objects, features, advantages and other possible modifications to the disclosed embodiments will become more fully apparent from the following detailed description, the appended claims and the accompanying drawings.

DETAILED DESCRIPTION

Figure 1:
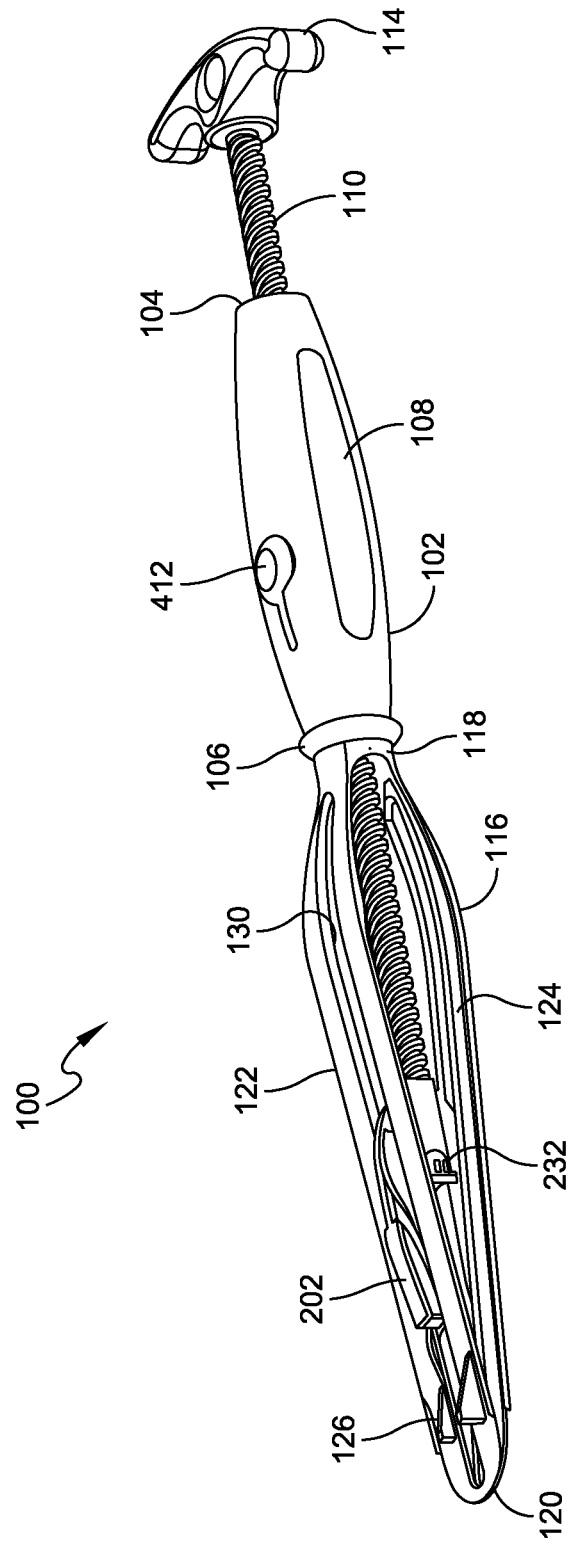
FIG. 1 is a perspective view of an anterior distractor-inserter according to one embodiment of the disclosure.

Embodiments presently disclosed generally relate to a distractor-inserter. More specifically, embodiments relate to an anterior distractor-inserter providing linear countersink depth adjustment. The countersink depth can be set to a value within a range of values, which may include more than two values. Adjustment may be analog, where any value within the range can be selected, or discrete, where whole values within the range can be selected stepwise. Embodiments may further include constant height retraction members. Further still, embodiments may include a ratchet mechanism that allows for automatic axial forward motion, but prevents axial backward motion unless the ratchet is manually disengaged.

A distractor-inserter is a device that can be used to distract (i.e., separate) two elements and insert another element therebetween. For example, in spinal surgery, a distractor-inserter may be used to separate two adjacent vertebral bodies and insert a spinal implant between the two separated vertebral bodies. The implant may be selected from a variety of implants, including without limitation, cages or spacers used to promote fusion, dynamic stabilization devices or artificial discs, and the like. The implants may be metal (e.g., titanium), or plastic (e.g., PEEK), or other biocompatible materials including other metals and/or plastics. Once inserted between two vertebral bodies, some spinal implants may ease pain by facilitating bone growth and fusion between the two vertebral bodies.

An embodiment of a distractor-inserter includes a head block assembly coupled to a distal end of a drive shaft, which can move the head block assembly forward and backward along a longitudinal axis of the distractor-inserter. The head block assembly is slidably disposed between two blades that can open at a distal end to separate two distractable elements, such as vertebral bodies. When the distal ends of the blades are positioned between the two distractable elements, forward movement (i.e., toward the distal ends) of the head block assembly cause the blades to open and thereby separate the two distractable elements.

According to various embodiments, the head block assembly includes a tip configured to push an implantable element toward the distal ends of the blades. After the distal ends of the blades have opened to separate the distractable elements, continued forward motion of the head block assembly causes the tip to push the implantable element beyond the open distal ends of the blades and into a space created between the two separated elements. When the tip is retracted from the space, the two separated elements engage the implantable element, thereby holding the implantable element in place between the separated elements.

According to one or more embodiments, the head block assembly includes retraction members above and below the tip. When the head block assembly is moved forward to its furthest extent, the retraction members engage with outer faces of at least one, and often both of the separated elements. Further forward force applied to the head block assembly causes the retraction members to push against the outer faces of the separated elements. The retraction members cause the tip to retract from between the separated elements when the retraction members push against outer faces of the separated elements.

In various embodiments, the location of the head block assembly tip is adjustable relative to the rest of the head block assembly to provide for adjustability of a countersink depth of the implantable element between the separated elements. More specifically, the distance between the tip and the retraction members is adjustable, and corresponds to the distance between the outer faces of the separated elements and the implantable element when the tip is fully extended into the space between the separated elements. The adjustable distance between the retraction elements and the tip therefore corresponds to the countersink depth of the implantable element.

According to at least one embodiment, the countersink depth can be adjusted linearly within a range of depths. In one embodiment, the range is zero millimeters to eight millimeters; however, other ranges are possible. In some embodiments selection of the countersink depth is discrete, wherein only whole values (e.g., nonfractional) can be selected. In other embodiments, selection of the countersink depth is analog, wherein any value (e.g., fractions of millimeters) within the range can be selected. Setting of the countersink depth to zero millimeters causes the implantable element to be positioned such that an outer face of the implantable element is substantially flush with at least one or both outer faces of the separated elements on either side of the implantable element.

Some embodiments include retraction members having constant height relative to outer faces of blades of the distractor-inserter. In these and other embodiments, the retraction members may be arms having faces that engage with respective faces of separated elements, such as vertebral bodies. The arms are anchored at a base portion of the head block assembly. The arms are disposed within, and guided by, channels in the blades. When the head block assembly moves forward and backward, the height of the arm faces remains generally constant, regardless of where the arms are along the length of the blades.

Figure 2:
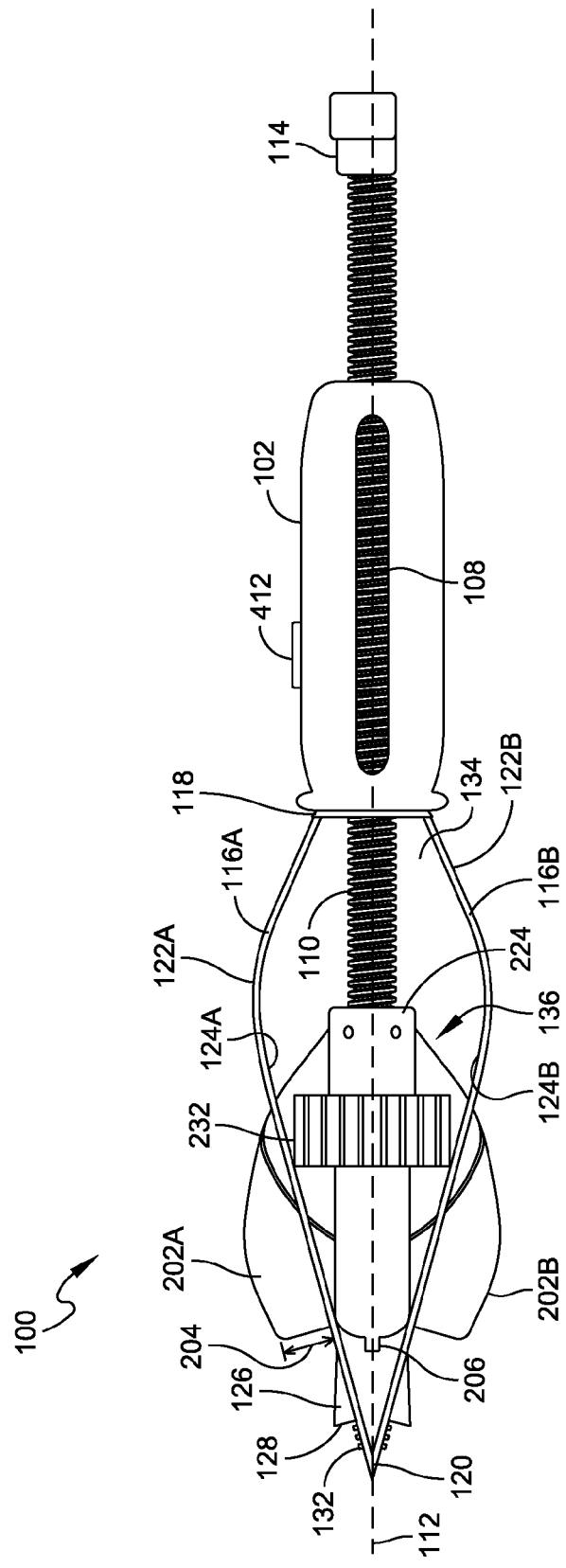
FIG. 2 is an elevation view of the distractor-inserter of FIG. 1.
Figure 3:
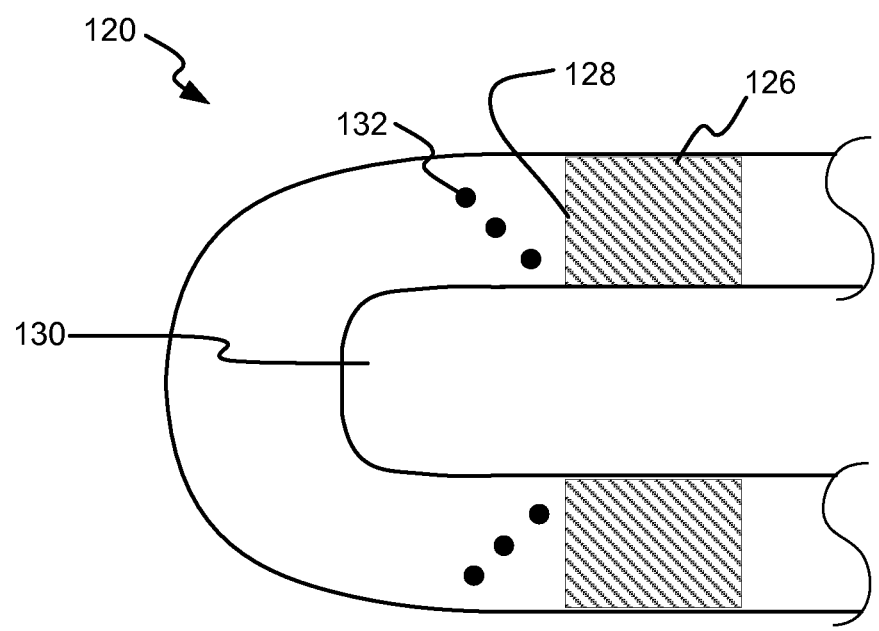
FIG. 3 is a plan view of a distal end of a blade of the distractor-inserter of FIG. 1.

FIG. 1 is a perspective view of an example distractor-inserter 100 according to one embodiment of the disclosure. FIG. 2 is an elevation view of the distractor-inserter 100. FIG. 3 is a plan view of a distal end of blades of the distractor-inserter 100. For ease of discussion, FIGS. 1-3 are referenced together in the following description.

The distractor-inserter 100 includes a handle 102 which enables a user to hold the distractor-inserter 100 during use. Handle 102 has a proximate end 104 and a distal end 106. The handle 102 forms a passage 108 (seen through a cut-out portion of the handle 102) extending through the length of the handle 102. In the illustrated embodiment, distractor-inserter 100 includes a drive shaft 110 extending through the passage 108 formed by the handle 102. Accordingly, the passage 108 may be a substantially cylindrical shape, or some other shape that is capable of receiving a cylindrically shaped member, such as drive shaft 110.

Handle 102 and drive shaft 110 are disposed along a longitudinal axis 112 that extends the length of the distractor-inserter 100. A grip 114, such as the illustrated "T" grip, is connected to a proximate end of drive shaft 110. The drive shaft 110 is slidably disposed through passage 108 of handle 102, such that the shaft 110 can be driven in a forward motion and a backward motion along the longitudinal axis 112, using the grip 114.

Connected to the distal end 106 of handle 102 are first and second blades 116. In the illustrated embodiment, first and second blades 116 are opposing. Opposing blades 116 have respective proximate ends 118 and distal ends 120. Opposing blades 116 have respective outer faces 122, facing away from the longitudinal axis 112, and an inner faces 124, facing the longitudinal axis 112. In the illustrated embodiment, the blades 116 are substantially concave. For example, middle sections of the length of the blades 116, between the distal ends 120 and the proximate ends 118, are curved away from the longitudinal axis 112.

The blades 116 are constructed of a material that renders them relatively flexible, such that the blades 116 can be disposed in a separated position or an unseparated position. In a separated position, opposing inner faces 124 of the blades 116 are open (e.g., not in contact with each other) at the distal ends 120. In the unseparated position, the inner faces 124 of the blades 116 are typically closed (e.g., in contact with each other) at the distal ends 120.

First and second blades 116 include stop members 126 which are mounted on outer faces 122 of the blades 116 near the distal ends 120 of the blades 116 (see, e.g., FIG. 3). Each stop member 126 has an engagement face 128 that faces the distal end 120 of the blade 116. Each engagement face 128 is substantially perpendicular to the respective outer face 122 of the blade 116 that the stop member 126 is mounted on.

In the illustrated embodiment, the first and second blades 116 include respective elongate channels 130 extending at least a portion of the length of the blades 116. In one embodiment, a stop member 126 is mounted on each side of the elongate channel 130 of the respective blade 116. Stop members 126 may be arranged on the blades 116 in different arrangements than those shown, depending on the particular implementation.

During operation, each engagement face 128 of the stop members 126 engages (e.g., abuts) a face of a distractable element, such as a vertebral body, which is to be separated. Stop members 126 may engage the face of one or both distractable elements depending on, for example, the shape of the distractable element faces, the position of the distractable elements, the surrounding tissue, as well as other factors. The engagement faces 128 thereby allow only a distal portion of each blade 116 to extend between the distractable elements (e.g., vertebral bodies). Specifically, the portions of the blades 116 allowed to extend between the separated elements extend from the furthest distal ends 120 of the blades 116 to the engagement faces 128 of the stop members 126. The stop members 126 may be any of numerous shapes and sizes, depending on the particular implementation, preferably to facilitate minimal contact with bodily structures (e.g., organs or vasculature) around the vertebral bodies (e.g., superior and inferior vertebrae).

With further regard to the blades 116, distal ends 120 further include friction elements 132. Friction elements 132 engage interior faces of distractable elements, such as the end plates of vertebral bodies. The friction elements 132 help stabilize the distal ends 120 of the blades 116 between the vertebral bodies during operation, by creating a friction force between the blades 116 and the vertebral bodies. In the illustrated embodiment, the friction elements 132 include a number of raised elements, such as bumps. Bumps are merely one example of types of friction elements that can be employed. Other embodiments may employ other friction elements such as serrations.

The bumps 132 (or other types of friction elements) may be beneficially oriented on outer faces 122 of the blades 116 in ways that correspond to the general shape or curvature of typical vertebral bodies (or other distractable elements). Such orientations of friction elements 132 may facilitate stabilization of the blades 116 between vertebral bodies better than orientations that do not correspond to the shapes or curvatures of the vertebral bodies. For example, in the illustrated embodiment, bumps 132 are disposed substantially diagonally from near the channel 130 distally outward toward the outer edges of the blades 116. In some embodiments, bumps 132 are in a curved orientation that may generally match a portion of the vertebral body. For example, in a particular embodiment bumps 132 are positioned to generally align with the apophyseal ring of a vertebral body. Although three bumps 132 are shown on each side of the channel 130 (see, e.g., FIG. 3), it is to be understood that any number of bumps 132 (or other types of friction elements) can be employed to achieve different results.

Referring again to the blades 116, the concavity of the blades 116 forms a space 134 between the inner faces 124 of the blades 116. The distal end of the drive shaft 110 extends into the space 134. A head block assembly 136 is mounted at the distal end of the drive shaft 110. The head block assembly 136 provides for retraction of the distal ends 120 of the blades 116 from separated elements and countersink depth adjustment, and is discussed in further detail below with reference to FIGS. 4-7.

Figure 4:
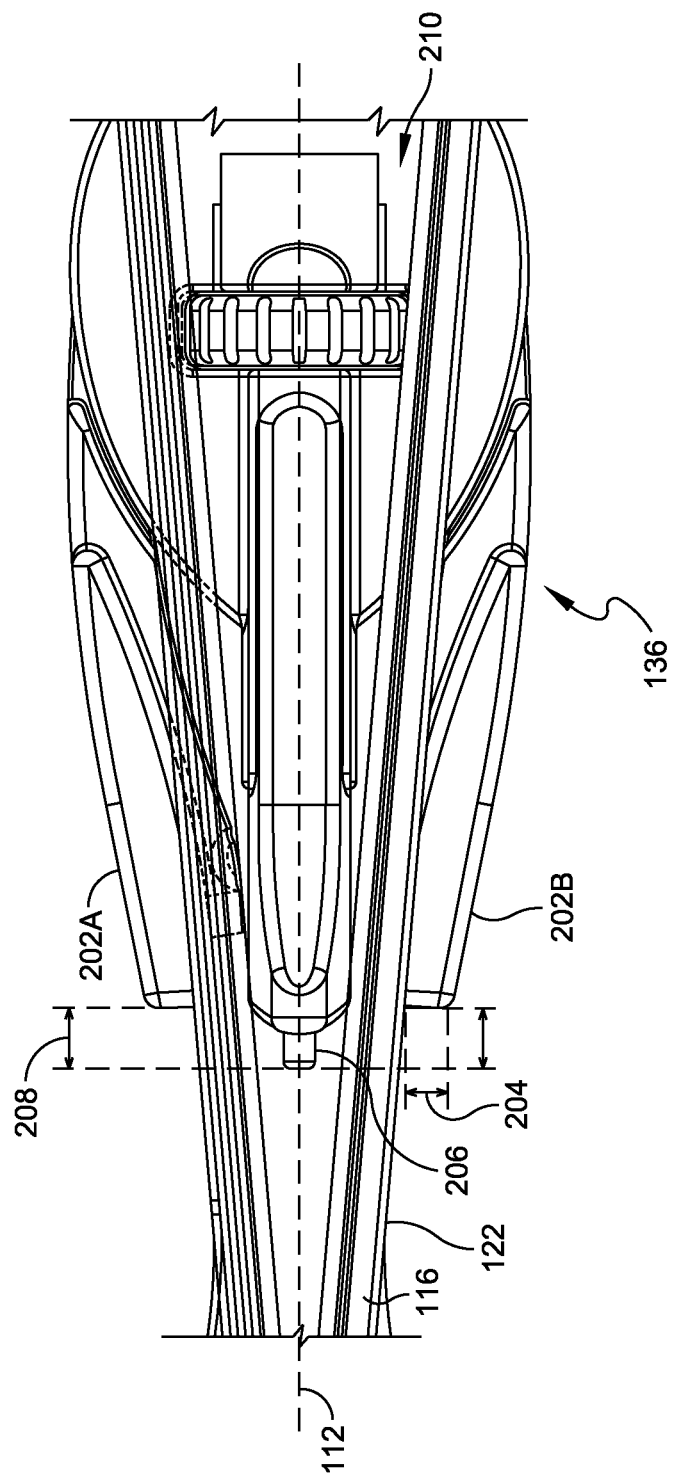
FIG. 4 is a cross sectional elevation view of a head block assembly of the distractor-inserter of FIG. 1.

Turning to FIG. 4, a cross-sectional elevation view of head block assembly 136 is shown. The head block assembly 136 includes two retraction members, such as upper and lower elongate arms 202. The head block assembly 136 is positioned between the blades 116 such that the arms 202 project laterally away from the longitudinal axis 112 and extend through respective elongate channels 130 of the blades 116. The channels 130 form tracks that guide the respective arms 202 as the head block assembly 136 moves forward (toward the distal ends 120) and backward (toward the handle 102) on the drive shaft 110. Arms 202 have height 204 that remains constant relative to the outer faces 122 of the respective blades 116. By maintaining a generally constant height 204 of arms 202 relative to outer faces 122 of blades 116, arms 202 engage tissue surrounding the disc space at a known orientation and position. Such a feature may be particularly useful when implanting into a small or short disc space, to help arms 202 avoid significant contact with soft tissue, vessels, and the like.

A tip 206 is disposed at a distal end of the head block assembly 136. The tip 206 is configured for pushing an implantable element toward the distal ends 120 of the blades 116 as the head block assembly 136 is driven forward by the drive shaft 110. When the distal ends 120 are opened, a space is created between two separated elements and the tip 206 pushes the implantable element between the two separated elements. A substantially longitudinal offset 208 between the tip 204 and the arms 202 corresponds to a countersink depth at which the implantable element is inserted.

The head block assembly 136 includes a countersink depth adjustment mechanism 210 for adjusting the offset 208 corresponding to the countersink depth of an implanted element. In one embodiment the countersink depth adjustment mechanism provides for linear adjustment of the countersink depth within a range of countersink depths. An embodiment of the countersink depth adjustment mechanism is shown in FIGS. 5-7 and is discussed in further detail below.

Figure 5:
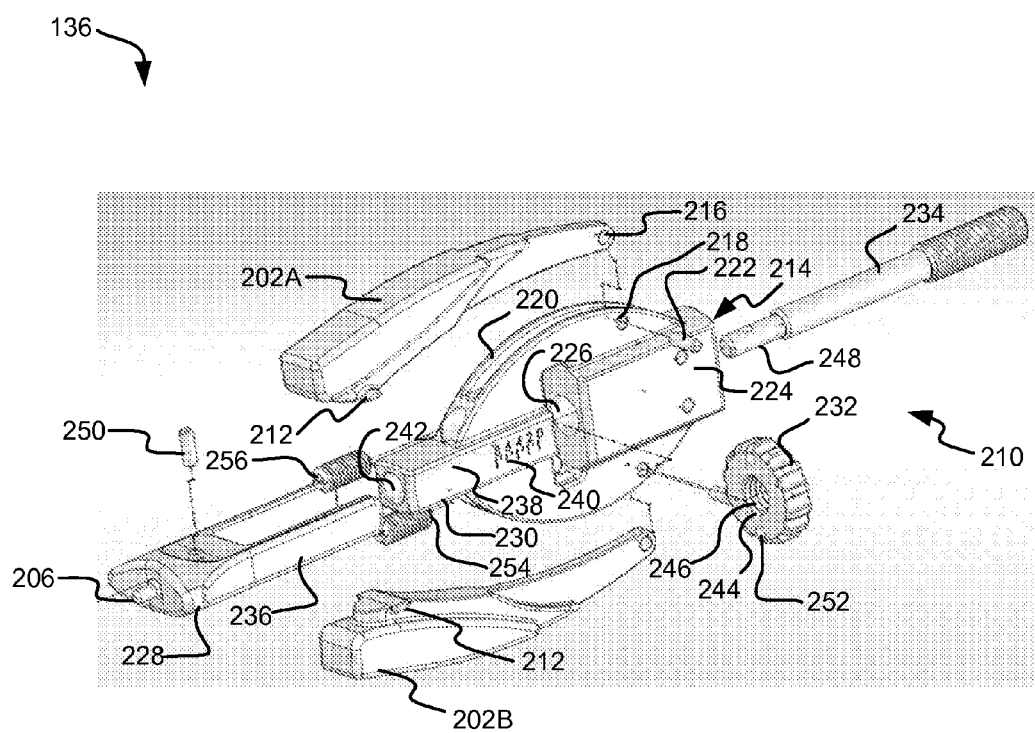
FIG. 5 is an exploded perspective view of the head block assembly including a countersink adjustment mechanism according to an embodiment.

FIG. 5 is an exploded perspective view of the head block assembly 136 according to one embodiment. In the view of FIG. 5, the countersink depth adjustment mechanism 210 is also exploded. With further regard to the arms 202, each arm 202 includes a rider member 212. Rider members 212 stabilize the arms 202 within the channels 130 of respective blades 116 and facilitate sliding of the arms 202 longitudinally forward and backward along the lengths of the blades 116. Rider members 212 facilitate maintaining constant height 204 of the arms 202 as the arms 202 slide along the blades 116.

The head block assembly 136 further includes a buttress 214 configured for anchoring the arms 202 and the drive shaft 110 within the distractor-inserter 100. Proximate ends of the arms 202 include coupling members 216 for coupling to a coupling point 218 of the buttress 214. The buttress 214 further includes upper and lower arced slots 220 into which bottom portions of respective elongate arms 202 fit. The coupling members 216 align with the coupling point 218 when the arms 202 are in the respective arced slots 220. When coupling members 216 and the coupling point 218 are aligned, fasteners, such as pins 222, are inserted therethrough to anchor the arms 202 to the buttress 214.

The buttress 214 further includes a core member 224 to which the distal end of the drive shaft 110 can be coupled. Coupling of the drive shaft 110 to the core member 224 is discussed in further detail below with reference to FIG. 8. In the illustrated embodiment, the core member 224 has a longitudinally disposed passage 226 formed therethrough. Core member passage 226 is discussed in further detail below with reference to the countersink depth adjustment mechanism 210.

In the illustrated embodiment the countersink depth adjustment mechanism 210 generally includes a countersink adjustment member 228, a countersink adjustment member carriage 230, a countersink adjustment interface member 232 and a countersink adjustment shaft 234. The countersink adjustment mechanism 210, and components thereof, are generally disposed along the longitudinal axis 112 of the distractor-inserter 100.

In one embodiment, the countersink adjustment member 228 is an elongate member having a distal end and a proximate end. The tip 206 is integrated on the distal end of the countersink adjustment member 228. The proximate end of the countersink adjustment member 228 is configured to slidably couple to the countersink adjustment member carriage 230. In one embodiment, the countersink adjustment member carriage 230 is integrated with the buttress 214. Once coupled to the countersink adjustment member carriage 230, the countersink adjustment member 228, including the tip 206, can move forward and backward relative to the countersink adjustment member carriage 230.

In the illustrated embodiment, the countersink adjustment member 228 includes sleeves 236. Sleeves 236 of the countersink adjustment member 228 fit over opposite sides 238 of the countersink adjustment member carriage 230 to engage the opposite sides 238 and provide sliding movement. As discussed in further detail below, the sleeves 236 expose countersink depth markings 240 on the countersink adjustment member carriage 230 as the sleeves 236 move forward, and cover the markings 240 as the sleeves 236 move backward. In this manner, the sleeves 236 and the markings 240 visibly indicate the current countersink depth setting.

In the illustrated embodiment, the countersink adjustment member carriage 230 has a passage 242 formed therethrough. The countersink adjustment interface 232 also has a passage 244 formed therethrough. The core member passage 226, the carriage passage 242 and the interface member passage 244 are aligned with the longitudinal axis 112. The countersink adjustment shaft 234 is generally an elongate member aligned with the core member passage 226, the carriage passage 242 and the interface member passage 244. When assembled, the countersink adjustment shaft 234 is positioned through the core member passage 226, the carriage passage 242 and the interface member passage 244.

In the illustrated embodiment, an interior surface 246 of the countersink adjustment interface member 232 that forms the passage 244 is threaded. A proximate end of the countersink adjustment shaft 234 is also threaded. When assembled, a portion of the threads of the countersink adjustment shaft 234 engage with the threads of the interior surface 246 of the interface passage 244. Actuation of the countersink adjustment interface member 232 thereby engages and actuates the countersink adjustment shaft 234.

In the illustrated embodiment the countersink adjustment interface member 232 is a thumbwheel that is rotatable about the countersink adjustment shaft 234. The thumbwheel 232 may have tactile members to facilitate rotary use of the thumbwheel. When the thumbwheel 232 is rotated, the threads of the interior surface 246 engage with the threads of the countersink adjustment shaft 234 and tend to push or pull the countersink adjustment shaft 234 longitudinally forward or backward, depending on the direction of rotation.

A distal end of the countersink adjustment shaft 234 includes a coupling member 248 configured to couple with the countersink adjustment member 228. In one embodiment, the coupling member 248 extends into a slot in the countersink adjustment member 228. A fastener, such as a pin 250, is disposed through the countersink adjustment member 228 and the coupling member 248 to thereby couple the countersink adjustment shaft 234 to the countersink adjustment member 228. Once coupled, the countersink adjustment member 228 tends to move in corresponding longitudinal motion with the countersink adjustment shaft 234 as the thumb wheel 232 is rotated.

In the illustrated embodiment, the thumbwheel 232 provides for a level of discrete selection of the countersink depth. The thumbwheel 232 includes one or more detent mechanisms to hold the thumbwheel 232 and countersink adjustment member 228, and thereby hold the countersink depth, at discrete values. For example, in some embodiments detent sockets 252 on the thumbwheel 232 face detent balls 254 of ball plungers 256. As the thumbwheel 232 is rotated, the detent balls 254 engage respective detent sockets 252 when they are in alignment and disengage from the detent sockets 252 when they are out of alignment. When the detent balls 254 are engaged, more force is needed to turn the thumbwheel 232 in order to disengage the detent balls 254 from the sockets 252.

In one embodiment, one or more detent sockets 252 are positioned radially at locations on the thumbwheel 232 that correspond to whole number unit offsets 208 (e.g., integer values of millimeters) between the tip 206 and faces of the arms. Detent sockets 254 may be located at other locations on the thumbwheel 232 to provide for fractional units of countersink depths (e.g., 1.5 mm, 1.8 mm, 2.2 mm, etc.).

In some embodiments, detent mechanisms are not included. In these embodiments, selection of the countersink depth is analog. The movement of the thumbwheel 232 in these embodiments is typically smooth and gradual. In these embodiments, the user can select virtually any depth within the range of depths.

Figure 6A:
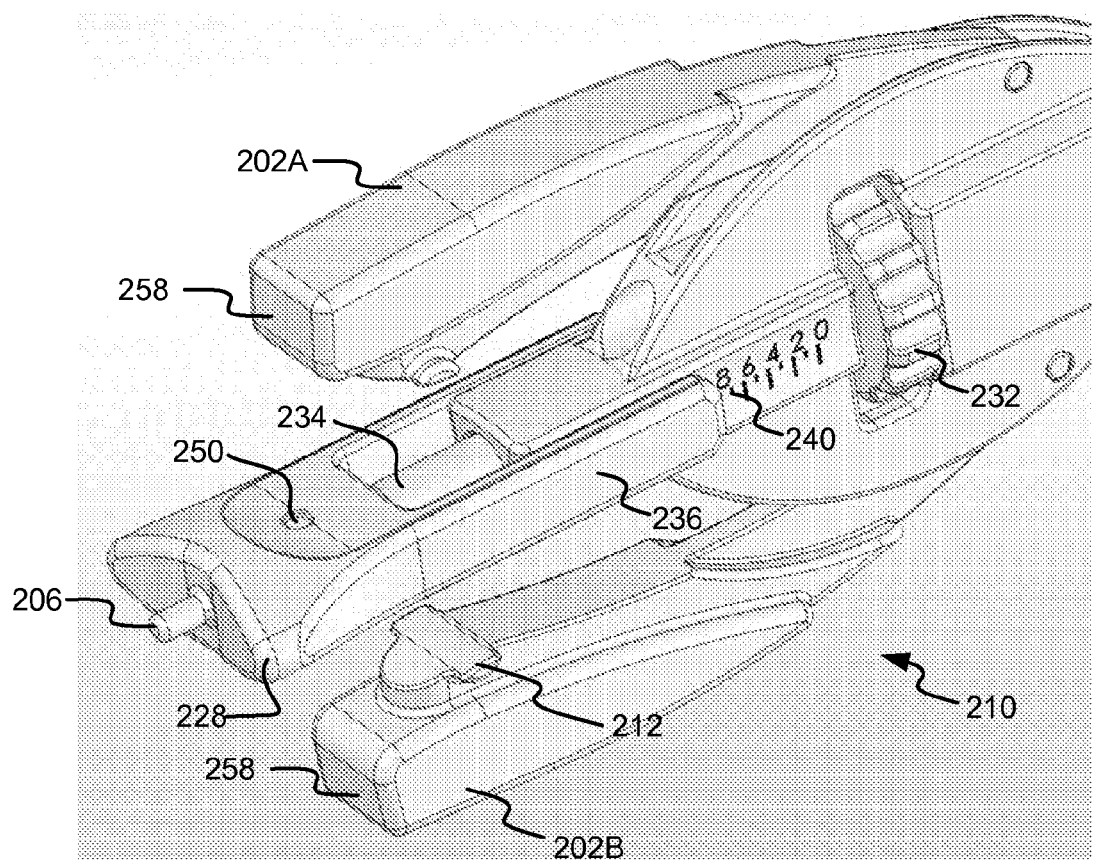
FIGS. 6A-6B are perspective views of the head block assembly including the countersink adjustment mechanism set to different countersink depth settings.
Figure 6B:
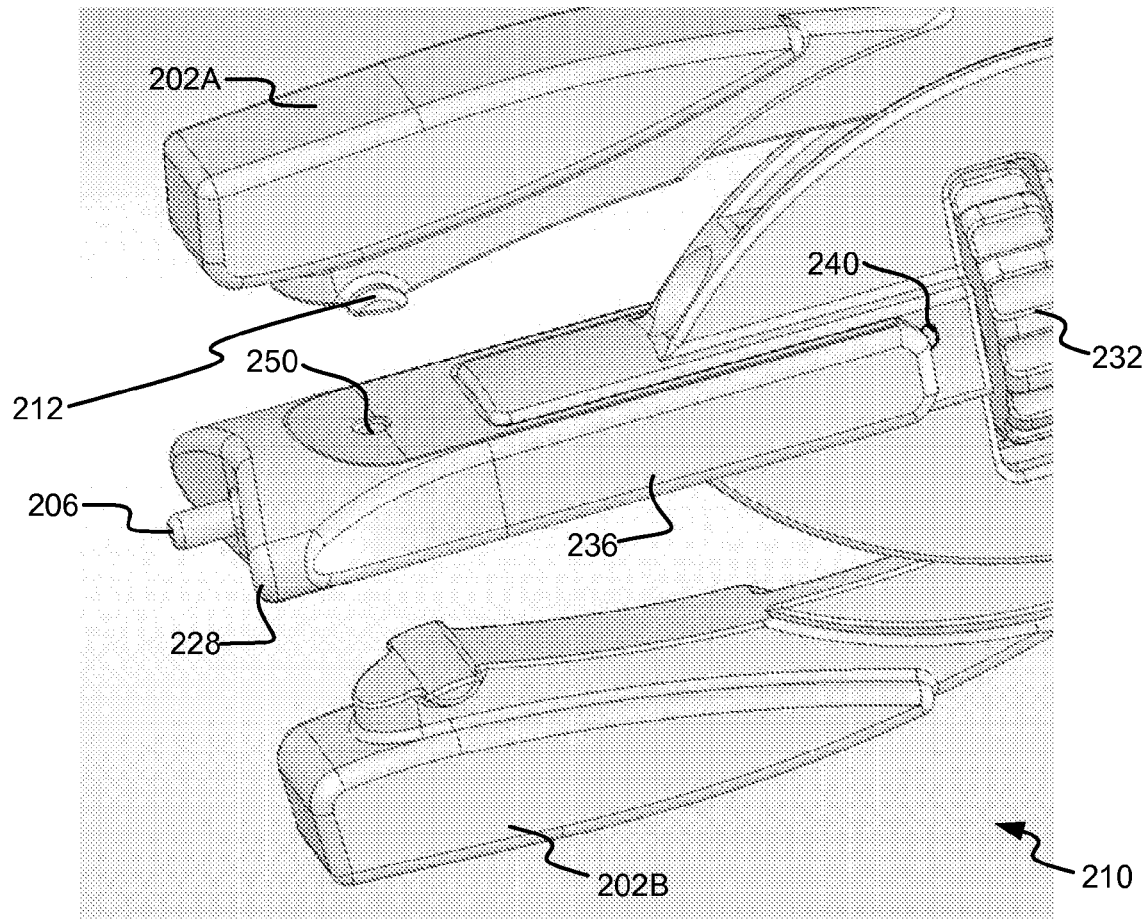

Turning to FIGS. 6A-6B, there are shown perspective views of the head block assembly 136, including the countersink depth adjustment mechanism 210 adjusted to two different countersink depths. In FIG. 6A, the countersink adjustment member 228 is in its furthest distal position. In this embodiment, the furthest distal position of the countersink adjustment member 228 corresponds to a countersink depth of eight millimeters, as indicated by the countersink depth markings 240. In FIG. 6B, the countersink adjustment member 228 is in its least distal position which corresponds to a countersink depth of zero millimeters, according to countersink depth markings 240. In other embodiments, the maximum countersink depth can be more or less than eight millimeters, and may be for example, six millimeters (6 mm), eight millimeters (8 mm), ten millimeters (10 mm), twelve millimeters (12 mm) or the like.

Figure 7A:
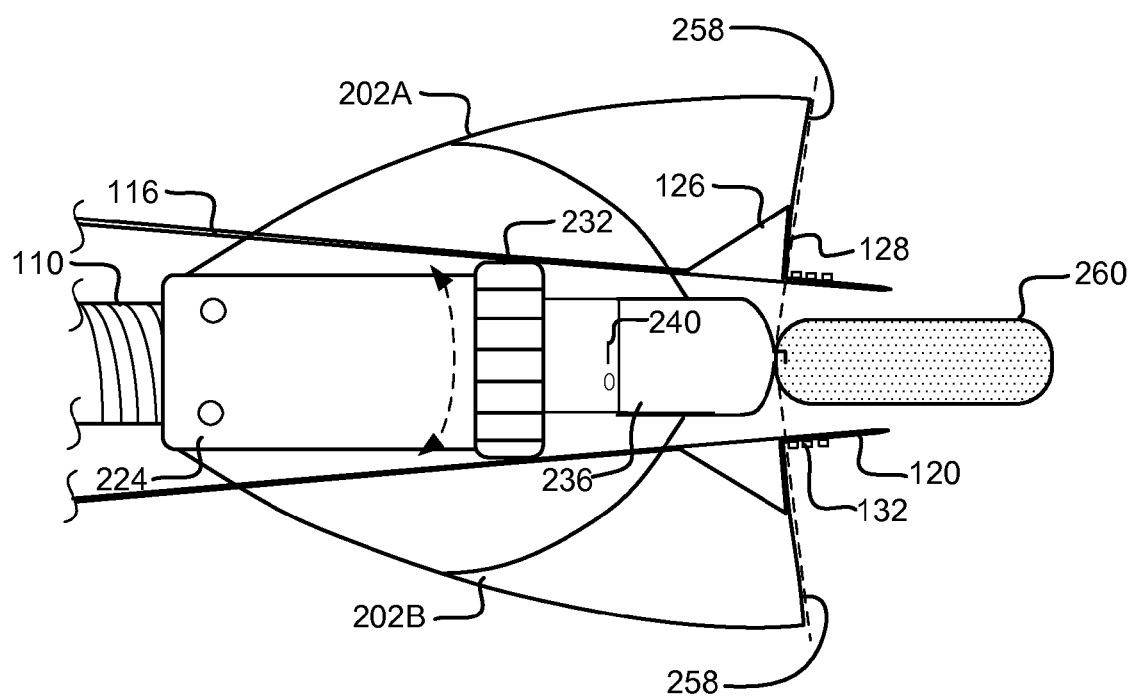
FIGS. 7A-7C are elevation views of the head block assembly between the blades, including the countersink adjustment mechanism set to different countersink depth settings.
Figure 7B:
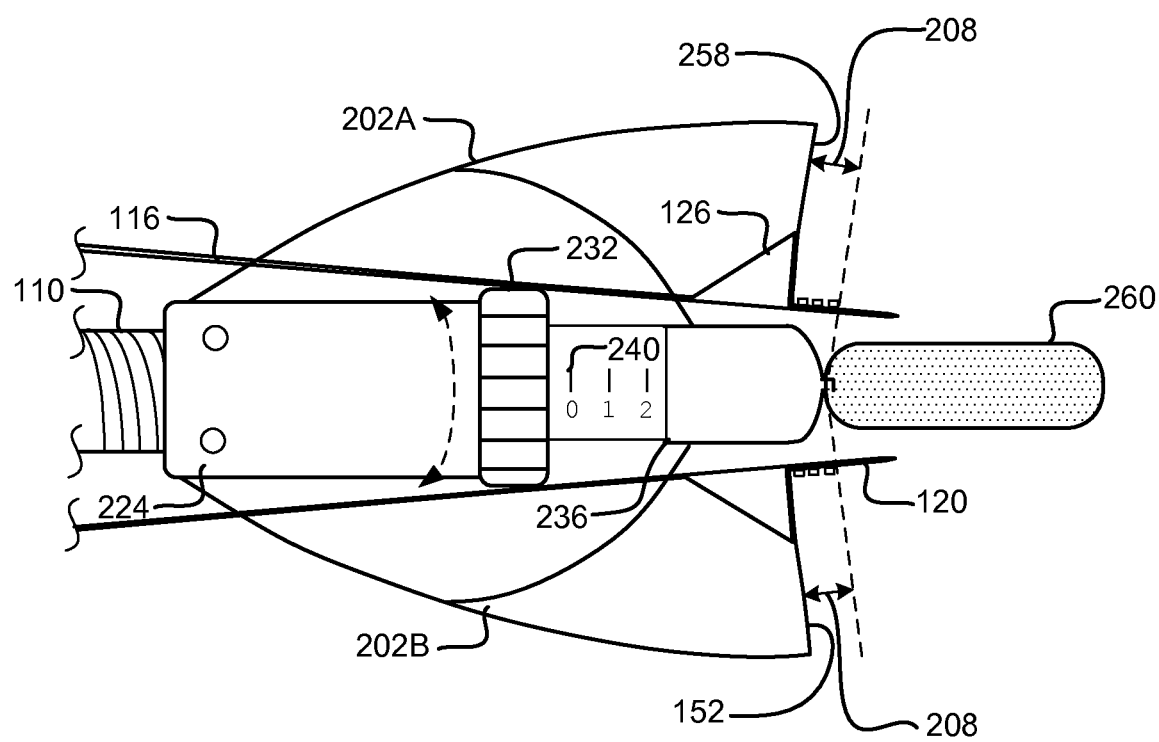
Figure 7C:
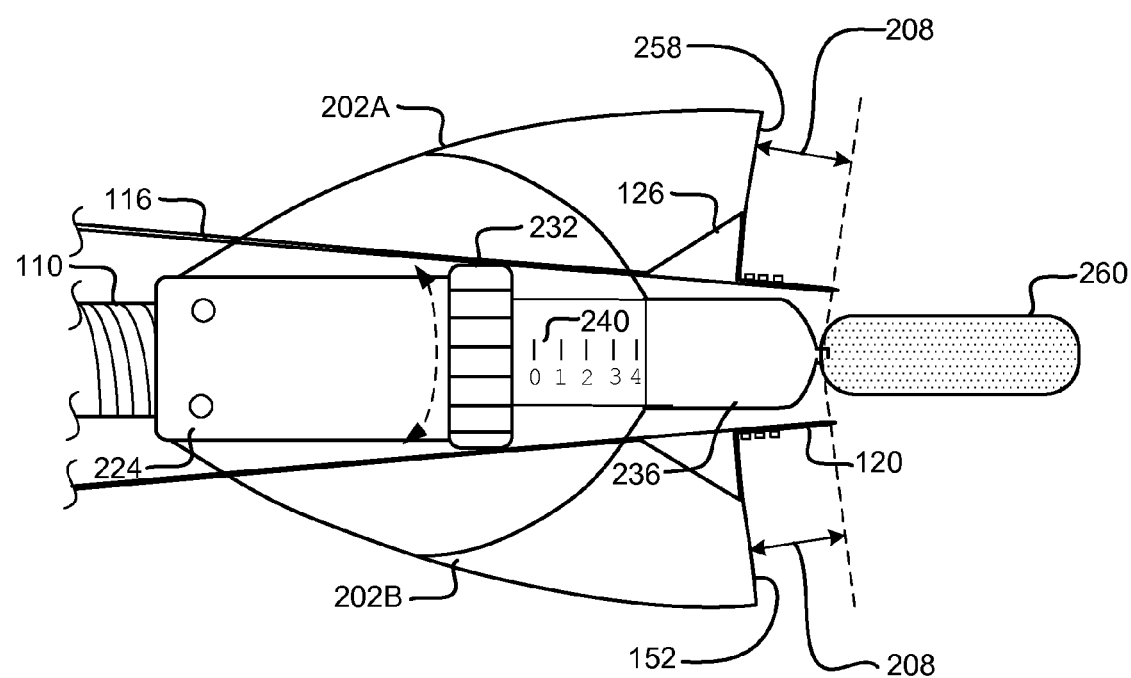

As discussed, the countersink adjustment mechanism 210 allows for linear adjustment of the countersink depth among a range of depths, which may include more than two depths. FIGS. 7A-7C are elevation views of the head block assembly 136 with the countersink depth set to three different depths. In FIG. 7A, the countersink depth is set to zero as indicated by depth marking 240. At zero countersink depth, the longitudinal distance 208 from the tip 206 to each face 258 of the arms 202 is zero millimeters. Zero millimeters of countersink depth corresponds to a flush alignment of an implantable element 260 when it is inserted between two distracted elements. Depending in part on the shape or irregularity of the faces of the distracted elements, the angle at which the distractor-inserter is positioned through tissue, and other factors, element 260 may be flush with only one of the distracted elements.

In FIG. 7B, the countersink depth is set to between two and three millimeters as indicated by markings 240. In some embodiments, the countersink depth can be set in an analog manner including fractions of depth units. The depth indicated by marking 240 corresponds to the distance 208 between the tip 206 and faces 258 of the retraction members 202, which in turn corresponds to the countersink depth of the implantable element 260. In FIG. 7C, the countersink depth is set to four millimeters as indicated by markings 240.

Figure 8:
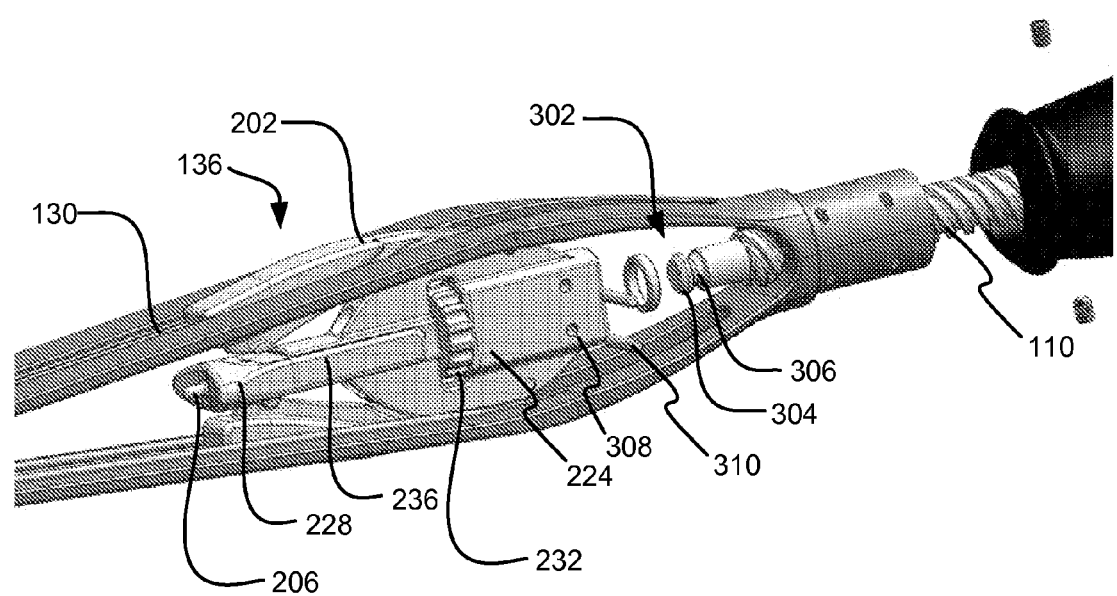
FIG. 8 is an exploded perspective view of a drive shaft coupling to the head block assembly according to one embodiment.

Turning to FIG. 8 there is shown a perspective view of an exploded coupling between the drive shaft 110 and the head block assembly 136. A distal end of the drive shaft 110 extends into the space 134 between the blades 116. The distal end of the drive shaft 110 includes a knob coupling member 302 including a knob 304 and recesses 306. The core member 224 of the buttress 214 includes an opening (not shown) on its proximal face.

When assembled, the knob coupling member 302 is inserted into the core member 224. Recesses 306 are aligned with coupling passages 308 of the core member 224. Fasteners, such as pins 310 are inserted through the coupling passages 308 and through the width of the core member 224. Within the core member 224, the pins 310 pass through the recesses 306 to engage the knob 304. In this configuration, the drive shaft 110 cannot be pulled out of the core member 224, but the drive shaft 110 can be twisted about the longitudinal axis 112. In alternative embodiments, coupling member 302 and core member 224 are connected together using other arrangements or mechanisms. For example, in one embodiment pins 310 may be replaced with a generally C-shaped clip. The C-shaped clip engages recesses 306 after knob 304 is place through a core member washer, such as that shown in FIG. 8. In this manner, drive shaft 110 and coupling member 302 are allowed to rotate relative to core member 224, but are axially connected to core member 224 in a way which provides axial movement of core member 224 as drive shaft 110 is advanced or retracted.

Figure 9:
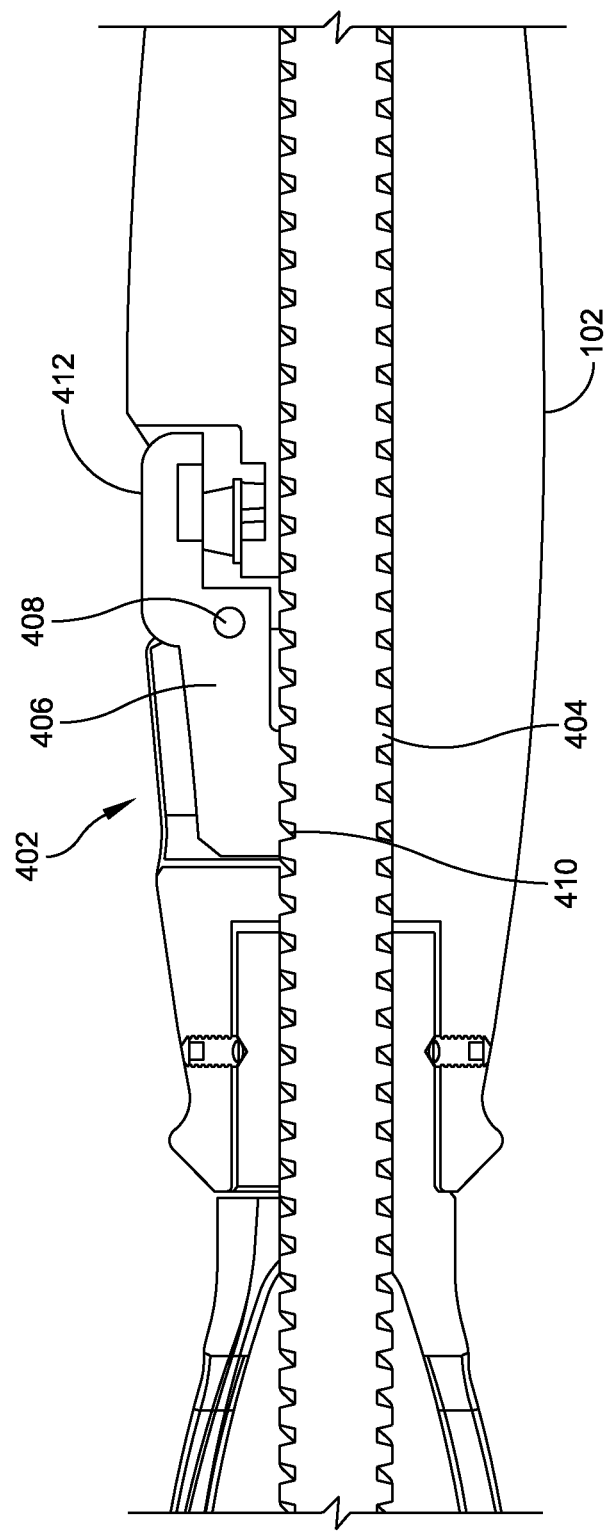
FIG. 9 is a cross sectional elevation view of a ratchet system of the distractor-inserter of FIG. 1 according to one embodiment.

Referring now to FIG. 9, there is shown a cross sectional elevation view of a ratchet system 402 of the distractor-inserter 100 according to one embodiment. In the illustrated embodiment, the shaft 110 is threaded. The threads 404 may comprise a leadscrew, such as a four leadscrew. The ratchet system 402 is configured to engage threads 404 of the shaft 110 as the shall 110 is pushed forward but prevent backward axial movement of the shaft 110 unless the ratchet is manually disengaged.

In one embodiment, the ratchet system 402 includes a ratchet arm 406 pivotally mounted on a pivot member, such as pivot pin 408. Catch members 410 are integrated on a bottom side of the arm 406 facing threads 404 of the shaft 110. Catch members 410 automatically insert between and catch threads 404, holding the drive shaft 110 in place. A ratchet disengagement button 412 is integrated on a top side of the pivot arm 406 and exposed on the surface of the handle 102. When the disengagement button 412 is depressed, the arm 406 pivots about the pivot pin 408, thereby raising the catch members 410 to disengage the threads 404 of the drive shaft 110.

In the illustrated embodiment, the drive shaft 110 cannot be pulled backward until the catches 410 are manually disengaged from the threads 404. The ratchet mechanism 402 thereby prevents the shaft 110 from moving backward, unless the user manually disengages the catch members 410. However, the coupling shown in FIG. 8 allows a user to twist the drive shaft 110 to cause backward movement as the threads 404 can slide in the thread direction through the catch members 410.

Figure 10:
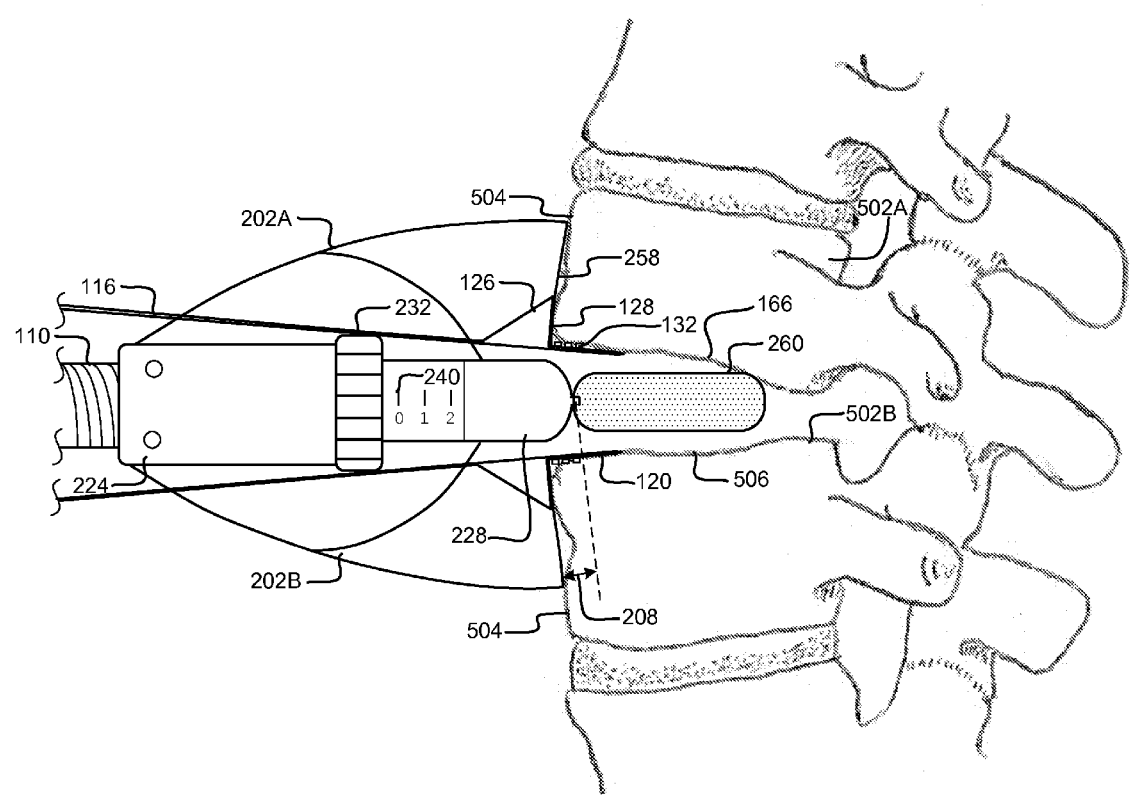
FIG. 10 is an elevation view of blades, head block assembly and countersink depth adjustment mechanism inserting an implant between adjacent vertebral bodies at a selected countersink depth.

Referring now to FIG. 10, there is shown an example use scenario in which a distractor-inserter is used to distract two vertebral bodies (superior vertebral body 502A and inferior vertebral body 502B) and insert a spinal implant 260 therebetween. In the illustrated scenario, the countersink adjustment member 228 has been set to provide a countersink depth of between 2 mm and 3 mm, as indicated by countersink depth markings 240. The distal ends 120 of the blades 116 are positioned between the superior vertebral body 502A and the inferior vertebral body 502B to points at which front faces 128 of the stop members 126 engage respective front faces 504 of the vertebral bodies 502. In addition, friction elements 132 engage respective interior faces 506 of the vertebral bodies 502.

In the illustrated use scenario of FIG. 5, the shaft 110 has been driven forward (toward the distal end 120) to push the head block assembly 136 forward, thereby separating the distal ends 120 of the blades 116 and the vertebral bodies 502. The head block assembly 136 is positioned at the furthest distal extent, where the faces 258 of the arms 202 engage respective faces 504 of associated vertebral bodies 502. In the illustrated position where the arm faces 258 engage the vertebral body faces 504, the implant 260 is between the vertebral bodies 502 at the selected countersink depth 208.

In the position illustrated in FIG. 5, as the shaft 110 is continued to be driven forward, the arm 202 faces 258 press against outer faces 504 of the vertebral bodies 502. The forward pressure of the arms 202 against the vertebral bodies 502 causes a backward, retractive force on the blades 116. The backward force causes the distal ends 120 of the blades, including the stop members 126 and the friction elements 132, to disengage from the vertebral bodies 502.

As the blades 116 disengage and retract from the vertebral bodies 502, the vertebral bodies 502 close together, applying compressive forces on upper and lower sides of the implant 260. The compressive forces on the implant 260 hold the implant 260 at the desired location between the vertebral bodies 502 while the blades 116 are retracted completely from between the vertebral bodies 502. Accordingly, the implant 260 becomes fixed between the vertebral bodies 502 as a result of the compressive force, and held at the selected countersink depth 208.

Figure 11:
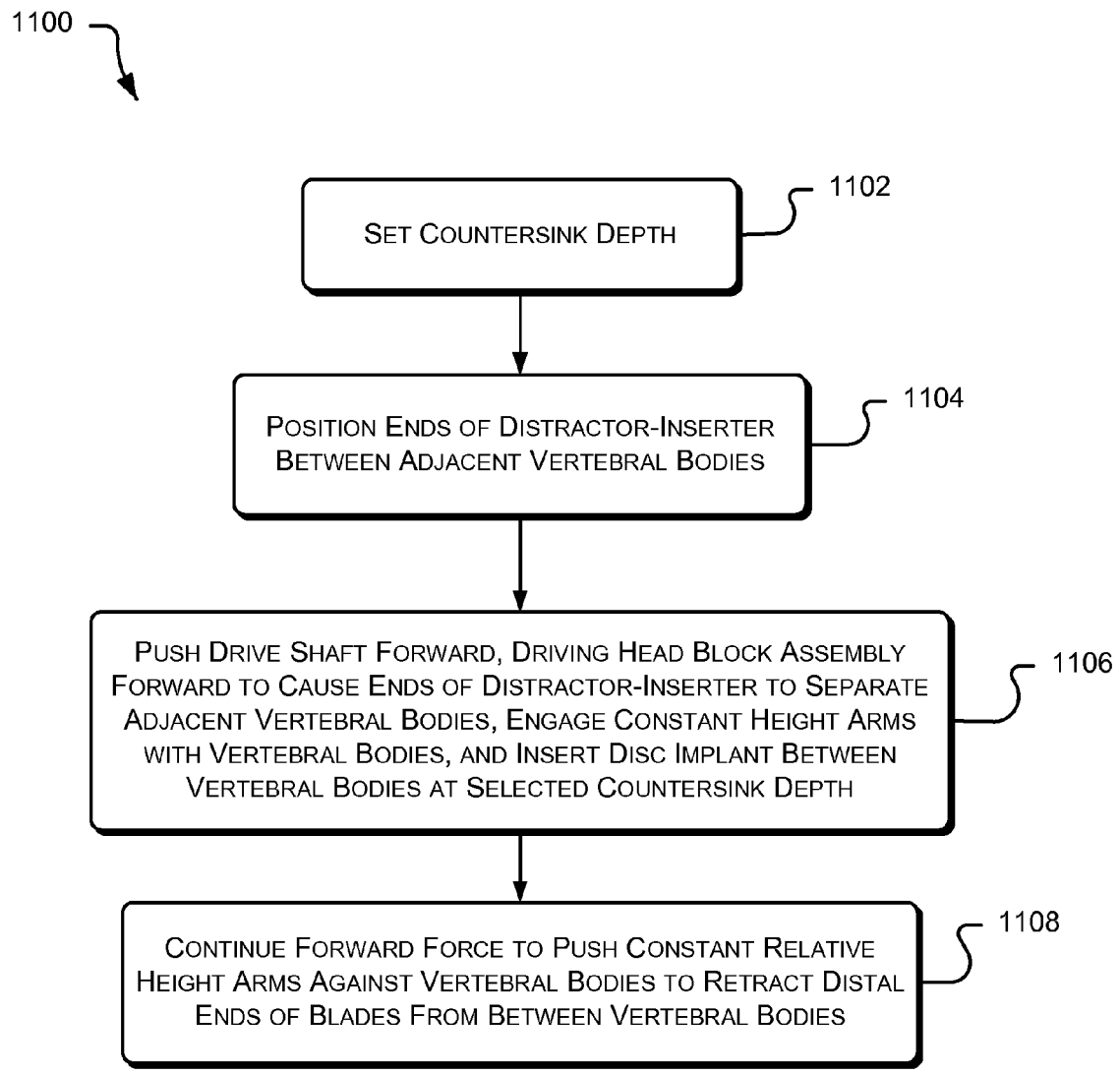
FIG. 11 is a flow diagram illustrating steps in a process of using a distractor-inserter in a distraction-insertion procedure according to an embodiment.

FIG. 11 is a flow diagram illustrating steps in a distraction-insertion process 1100 using a distractor-inserter, such as the distractor-inserter of FIG. 1, according to an embodiment. Following the process 1100 of FIG. 11, a linear countersink depth adjustment mechanism is adjusted to provide for a desired countersink depth (block 1102). In one embodiment, countersink adjustment involves turning a thumb wheel of the distractor-inserter, which causes a tip portion that pushes an implantable element, to move along a longitudinal axis toward or away from a reference point (e.g., retraction member faces) in a linear fashion.

In some embodiments, the countersink adjustment mechanism enables the user to select a countersink depth within a range of multiple countersink depths, which may be more than two countersink depths. In one embodiment, the range of countersink depths is zero millimeters (mm) to eight mm, but other ranges may be employed. In some embodiments, the movement may be graduated, wherein movement from one countersink depth to another is analog.

Continuing with the process 1100 of FIG. 11, distal ends of blades of the distractor-inserter are positioned (block 1104) between two elements to be separated, such as adjacent vertebrae of a spinal column. In one embodiment, the blades of the distractor-inserter are inserted in an anterior fashion, for example through the abdomen of a patient. According to an embodiment, stop elements of the blades engage respective front faces of the adjacent vertebrae, at which point the blades are prevented from going any deeper between the adjacent vertebrae.

In one embodiment, when distal ends of the blades are positioned (block 1104) between adjacent vertebrae, one or more friction elements on outer faces of the blades engage interior faces of the vertebrae. In this embodiment, the one or more friction elements may be arranged on the outer faces of the blades to substantially correspond to curvature of the end plates of the vertebrae.

Continuing with the process 1100 of FIG. 11, a shaft of the distractor-inserter is driven (block 1106) forward toward the distal ends of the blades until retraction elements (e.g., arms 202, FIG. 4) of a head block assembly engage respective outer faces of the vertebrae. Driving the head block assembly forward causes the distal ends of the blades to separate, thereby pushing the vertebral bodies apart. When the arms engage the outer faces of the vertebrae, the implantable element is positioned between the vertebrae at the selected (block 1102) countersink depth.

In the process 1100, continuing (block 1108) to drive the head block assembly forward causes arms of the head block assembly to push against the outer faces of the vertebral bodies. When the arms push against the vertebral bodies, the distal ends of the blades disengage from the vertebral bodies and allow for retraction of the blades from the spinal region. As the blades retract, the vertebral bodies come together and the implantable element is held between them. The compression forces imparted on the implantable element between the vertebral bodies causes the implantable element to disengage from the tip of the distractor-inserter and remain fixed at the selected countersink (block 1102) depth between the vertebral bodies.

In conclusion, various systems, devices, methods and arrangements for distraction and insertion are disclosed. While detailed descriptions of one or more embodiments have been provided above, various alternatives, modifications, and equivalents are possible. Therefore, the above description should not be taken as limiting the scope of possible embodiments, which is defined by the appended claims.

What is claimed is:

1. An apparatus for distracting two distractable elements and inserting an implantable element therebetween, the apparatus comprising:
   an elongate handle;
   first and second blades, the first and second blades having respective proximal ends that are connected to a distal end of the elongate handle, the first and second blades having respective distal ends configured to distract the two distractable elements;
   at least one stop member coupled to an outer face of at least one of the first and second blades;
   a longitudinally moveable drive shaft disposed through a passage formed by the elongate handle;
   a head block assembly mounted on a distal end of the drive shaft and disposed within a space formed between the first and second blades, the head block assembly including:
      a tip residing in a space defined by the first and second blades configured to push the implantable element to a selected depth between the distracted two distractable elements;
      first and second retraction members slidably disposed within respective first and second channels of the first and second blades, the first and second retraction members configured to maintain a constant height from the first and second blades, wherein the first and second retraction members are configured to engage respective outer faces of the distracted two distractable elements; and
   means for linearly adjusting a distance between the tip and the first and second retraction members to thereby linearly adjust a countersink depth of the implantable element between the distracted two distractable elements;
   wherein the means for linearly adjusting the distance between the tip and the retraction members comprises:
      a countersink member carriage having a first passage disposed therethrough along a longitudinal axis;
      a countersink member moveably coupled to the countersink member carriage the countersink member having a distal end comprising the tip;
      a thumbwheel having a second passage disposed therethrough along the longitudinal axis, the second passage having a threaded surface; and
      a countersink adjustment shaft disposed along the longitudinal axis and extending through the first passage and the second passage, the countersink adjustment shaft having a distal end coupled to the countersink member and a proximal end that is threaded;
      wherein threads of the second passage engage with threads of the countersink adjustment shaft, and wherein rotation of the thumbwheel causes longitudinal movement of the countersink adjustment shaft, and wherein longitudinal movement of the countersink adjustment shaft causes corresponding movement of the countersink member.

2. The apparatus of claim 1, wherein the distal end of the drive shaft is twistably coupled to the head block assembly.

3. The apparatus of claim 1, wherein the handle includes a ratchet mechanism configured to engage the drive shaft, the ratchet mechanism configured to permit linear or rotational forward movement of the drive shaft, and the ratchet mechanism configured to prevent linear backward movement of the drive shaft unless the ratchet mechanism is disengaged from the drive shaft.

4. The apparatus of claim 1, wherein the first and second retraction members remain at a constant height relative to the respective first and second blades as the first and second retraction members slide along a length of the respective first and second blades.

5. The apparatus of claim 1, wherein the countersink member carriage includes markings indicating a range of selectable countersink depths.

6. The apparatus of claim 5, wherein the countersink member comprises a sleeve around the countersink member carriage, and wherein the sleeve exposes the markings as the sleeve moves forward.

7. The apparatus of claim 1, wherein the distal end of at least one of the first and second blades has a friction element adapted to engage a face of one of the two distractable elements.

8. The apparatus of claim 7, wherein the friction element is shaped to generally match a shape of at least a portion of the face of at least one of the two distractable elements.

9. The apparatus of claim 8, wherein at least one of the two distractable elements comprises a vertebrae, and the face comprises an end plate of the vertebra.

* * * * *

UNITED STATES PATENT AND TRADEMARK OFFICE
CERTIFICATE OF CORRECTION

PATENT NO. : 8,540,724 B2
APPLICATION NO. : 12/771953
DATED : September 24, 2013
INVENTOR(S) : Mast et al.

It is certified that error appears in the above-identified patent and that said Letters Patent is hereby corrected as shown below:

In the Specification

Column 2, line 34, delete "shall." and insert -- shaft. --, therefor.

Column 2, line 46, delete "shall." and insert -- shaft. --, therefor.

Signed and Sealed this
Third Day of June, 2014

Michelle K. Lee
*Deputy Director of the United States Patent and Trademark Office*